(12) United States Patent
Fisher et al.

(10) Patent No.: US 6,526,802 B1
(45) Date of Patent: Mar. 4, 2003

(54) PORTABLE BREATH TEST SIMULATOR

(75) Inventors: David A. Fisher, Harrisburg, PA (US); Richard U. Guth, Harrisburg, PA (US)

(73) Assignee: Guth Laboratories, Inc, Harrisburg, PA (US)

( * ) Notice: Subject to any disclaimer, the term of this patent is extended or adjusted under 35 U.S.C. 154(b) by 60 days.

(21) Appl. No.: 09/894,716

(22) Filed: Jun. 28, 2001

(51) Int. Cl.[7] ............................................. G01N 33/497
(52) U.S. Cl. ........................... 73/1.03; 366/273; 436/9
(58) Field of Search ............................. 73/1.03, 1.04, 73/1.05, 1.06, 23.3; 366/273, 274; 422/84, 85, 86; 436/9

(56) References Cited

U.S. PATENT DOCUMENTS

| | | | |
|---|---|---|---|
| 3,647,397 A | 3/1972 | Coleman | 23/309 |
| 3,847,551 A * | 11/1974 | Hutson | 73/1.03 X |
| 3,854,319 A | 12/1974 | Burroughs et al. | 73/1 A |
| 3,948,604 A | 4/1976 | Hoppesch | 23/254 R |
| 4,040,605 A | 8/1977 | Towsend | 259/64 |
| 4,072,598 A | 2/1978 | Damgaard | 204/274 |
| 4,227,815 A | 10/1980 | Hoffa | 356/436 |
| 4,292,978 A | 10/1981 | Guth | 128/730 |
| 4,391,777 A * | 7/1983 | Hutson | 73/864.83 X |
| 4,407,152 A | 10/1983 | Guth | 73/1 G |
| 4,474,048 A | 10/1984 | Schmidt | 73/1 G |
| 4,911,555 A | 3/1990 | Saffer et al. | 366/274 |
| 4,978,863 A | 12/1990 | Lyons et al. | 250/574 |
| 5,134,875 A | 8/1992 | Jensen et al. | 73/1 G |
| 5,211,890 A | 5/1993 | Wentworth, Jr. | 261/30 |
| 5,246,632 A | 9/1993 | Wentworth, Jr. | 261/29 |
| 5,261,742 A | 11/1993 | Lockhart | 366/141 |
| 5,285,672 A | 2/1994 | Yao | 73/1 G |
| 5,326,166 A | 7/1994 | Walthall et al. | 366/165 |
| 5,552,324 A * | 9/1996 | Liu | 436/132 |
| 5,776,255 A | 7/1998 | Asaba et al. | 118/726 |
| 5,831,721 A | 11/1998 | Alkafeef | 356/70 |
| 6,096,558 A | 8/2000 | Stock | 436/132 |
| 6,109,780 A | 8/2000 | Lesniak | 366/253 |

* cited by examiner

Primary Examiner—Thomas P. Noland
(74) Attorney, Agent, or Firm—Hooker & Habib, P.C.

(57) ABSTRACT

A portable breath test simulator including a case having a jar support arm extending to one side of the top of the case. A jar containing a known water-alcohol solution is mounted on the bottom of the arm. The case and jar support the simulator. A magnetic power drive located in the case to one side of the jar rotates a magnetic stirrer in the jar. Breath blown into the jar forms an effluent having a known concentration of alcohol and is flowed to a breath test analyzer to be tested.

15 Claims, 3 Drawing Sheets

PORTABLE BREATH TEST SIMULATOR

FIELD OF THE INVENTION

The invention relates to simulators for supplying a breath test analyzer with an effluent having a preciously controlled concentration of ethyl alcohol. The effluent is used to calibrate a breath test analyzer prior to conducting breath tests to determine the concentration of alcohol in the breath of a subject and, indirectly, the amount of alcohol in the subject's blood. Breath tests are commonly used to determine whether the subject has violated a drunk driving law.

DESCRIPTION OF THE PRIOR ART

Breath test analyzers are commonly used to determine the breath alcohol of vehicle operators. Some analyzers are sophisticated, very accurate and reliable. These analyzers are not easily portable. Other types of breath test analyzers include small handheld units used for initial screening of drunk driving suspects by police officers and breath test analyzers forming parts of automobile interlock systems used to prevent use of an automobile until the driver passes a breath test. These analyzers must be frequently tested for accuracy using a breath test simulator and adjusted appropriately based on the test. For instance, in some states, the breath test analyzers used in auto interlock systems must be tested every two weeks.

Testing of breath test analyzers is facilitated by use of a portable breath test simulator which can be easily transported to the breath test analyzer to conduct a test. Portable breath test simulators should be capable of being transported wherever the operator goes over the highways and, even, on airplanes.

A conventional portable breath test simulator uses a compressed nitrogen gas-alcohol solution held under high pressure in a pressure tank. This simulator cannot be transported through roadway tunnels or by airplanes. Further, the accuracy of test conducted using this portable simulator is affected by the humidity of the ambient environment so that a humidity calculation is required during each test. Sometimes, the pressure tank must be warmed to prevent condensation in the charged vapor.

Thus, there is a need for an improved portable breath test simulator which is transportable with the operator without spills or leaking, through roadway tunnels and even by air and which generates a breath test effluent having a known concentration of ethyl alcohol for accurately calibrating breath test analyzers of all types. The portable breath test analyzer should be stable when mounted on a horizontal surface to reduce accidental tipping and should tightly confine the solution used for generating effluent against spilling. The chamber containing the solution should be sealed both to prevent the spilling in case of an upset and to prevent alcohol vapor from escaping into the simulator. The simulator should be self powered for use at field locations away from a conventional power outlet and should also be capable of operation by vehicle battery or conventional 120 volt AC electric power. The operator of the portable breath simulator should be able to replace depleted solution with new solution as required to permit extended field use of the simulator.

SUMMARY OF THE INVENTION

The invention is an improved portable breath test simulator using a water-alcohol solution to generate a breath test effluent. When the portable breath test simulator is not in use, the water-alcohol solution is confined within an entirely sealed jar to prevent leakage. The simulator has a stable construction which reduces the likelihood of upset during transport. The simulator is light weight and easily manually transported to a breath test analyzer to be calibrated. For instance, the portable simulator is easily carried by the operator to a vehicle fitted with a breath test auto interlock in order to test the breath test analyzer in the interlock.

The water-alcohol solution used by the portable breath test simulator is contained in a disposable jar which is removably mounted on the simulator. After depletion of the alcohol in the solution, the jar is removed from the simulator and a jar containing a fresh water-alcohol solution is mounted on the simulator by the operator to permit continued field use of the simulator.

The simulator includes a rechargeable battery power supply permitting use of the simulator at any desired location. Additionally, the simulator includes a mechanical stirrer which moves the solution in the jar past a heater in order to assure that all solution is maintained at the desired temperature and the water-alcohol solution is well mixed. The stirrer includes driven magnets which are rotated by drive magnets rotated in turn by an electric motor. The drive magnets and motor are located outside and to one side of the jar so that the magnetic field extending from the drive magnets to the driven magnets extends through one side of the solution jar. Locating the magnetic drive adjacent one side of the jar means that the jar can be located at the bottom of the simulator to support the simulator. This arrangement reduces the height of the simulator and increases stability of the simulator because the magnetic drive does not have to be located below the jar. The portable breath test simulator operates independently of barometric pressure.

Other objects and features of the invention will become apparent as the description proceeds, especially when taken in conjunction with the accompanying drawings illustrating the invention, of which there are three sheets of drawings and one embodiment.

DESCRIPTION OF THE PREFERRED EMBODIMENT

Figure 1:
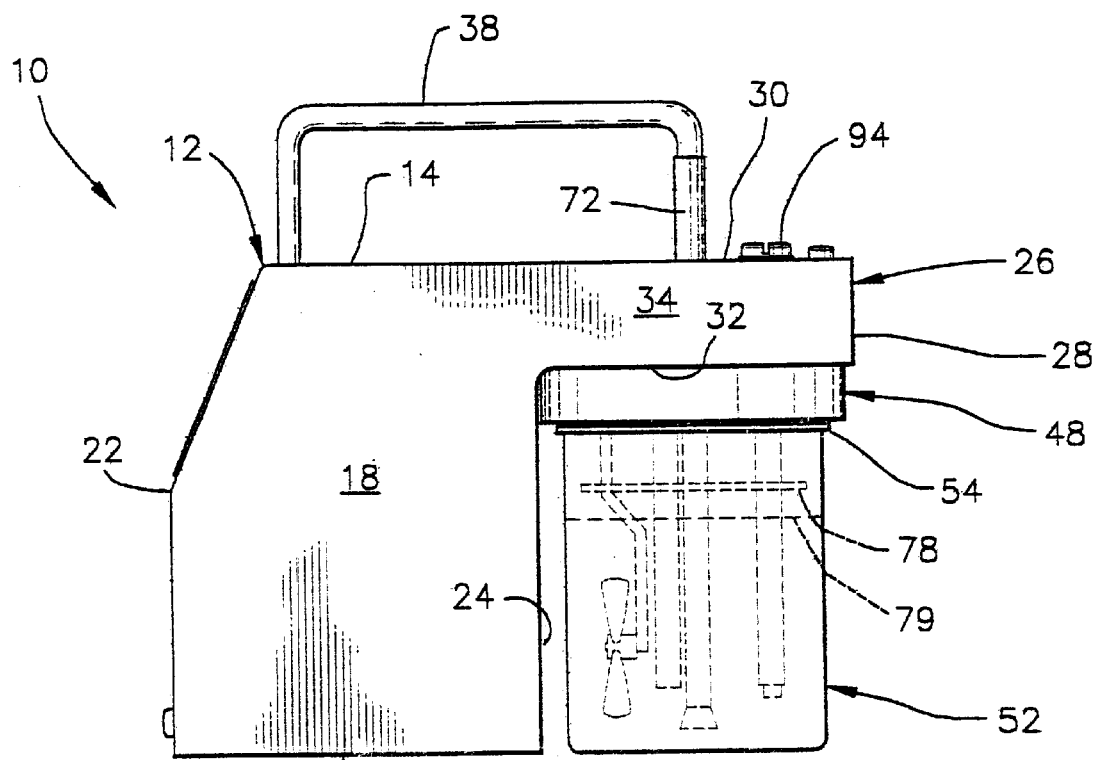
FIGS. 1, 2 and 3 are side, rear and top views of a simulator according to the invention.
Figure 2:
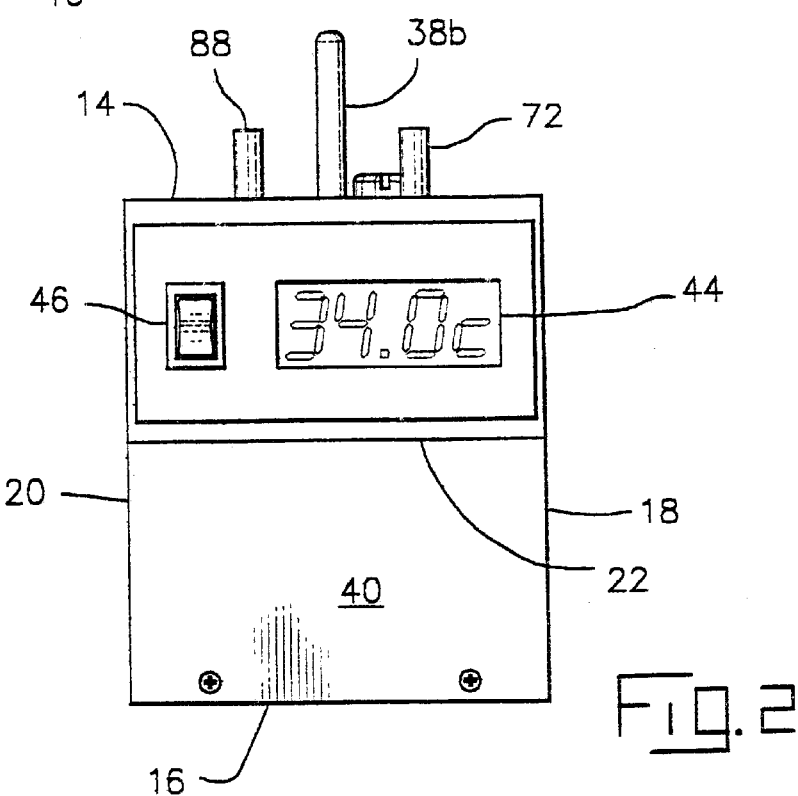
Figure 3:
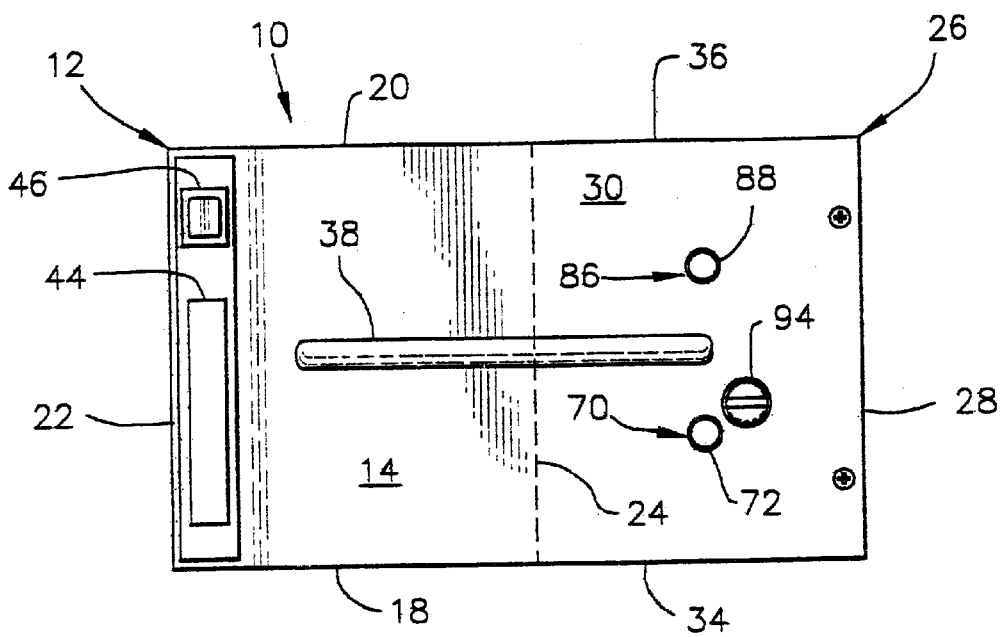

The simulator disclosed herein relates to the simulator of Guth, U.S. Pat. No. 4,407,152, the disclosure of which is incorporated herein by reference, in its entirety.

Portable breath simulator 10 includes a metal case 12 formed from sheet aluminum having a top 14, a bottom 16, opposed sides 18 and 20, back wall 22 and front wall 24. The case includes a jar support arm 26 located at the top of the case and extending forwardly from front wall 24. Arm 26 includes an arm front 28, parallel to and spaced outwardly from front 24, arm top 30, coplanar with top 14, arm bottom 32 parallel to top 30 and located a distance below top 30, and arm sides 34 and 36, forming extensions of sides 18 and 20, respectively.

Handle 38 is mounted on the top of the case. Handle 38 has a pair of spaced, vertical portions 38a and 38b and a horizontal grip portion 38c above top 14 and extending between the upper ends of the vertical portions, parallel to the top of the case. Vertical portion 38a is secured to case top 14. Vertical portion 38b is secured to arm top 30. The center of gravity of simulator 10, including the battery and the filled solution jar mounted on the arm, is located below the center of the grip portion to facilitate lifting and transport of the simulator. The sides, top and bottom of case 12 are flat and extend horizontally or vertically. Back wall 22 includes a vertical lower portion 40 and an angled upper proportion 42 bearing a solution temperature display unit 44 and on/off switch 46. Upper portion 42 is angled to facilitate viewing of display 44.

Figure 4:
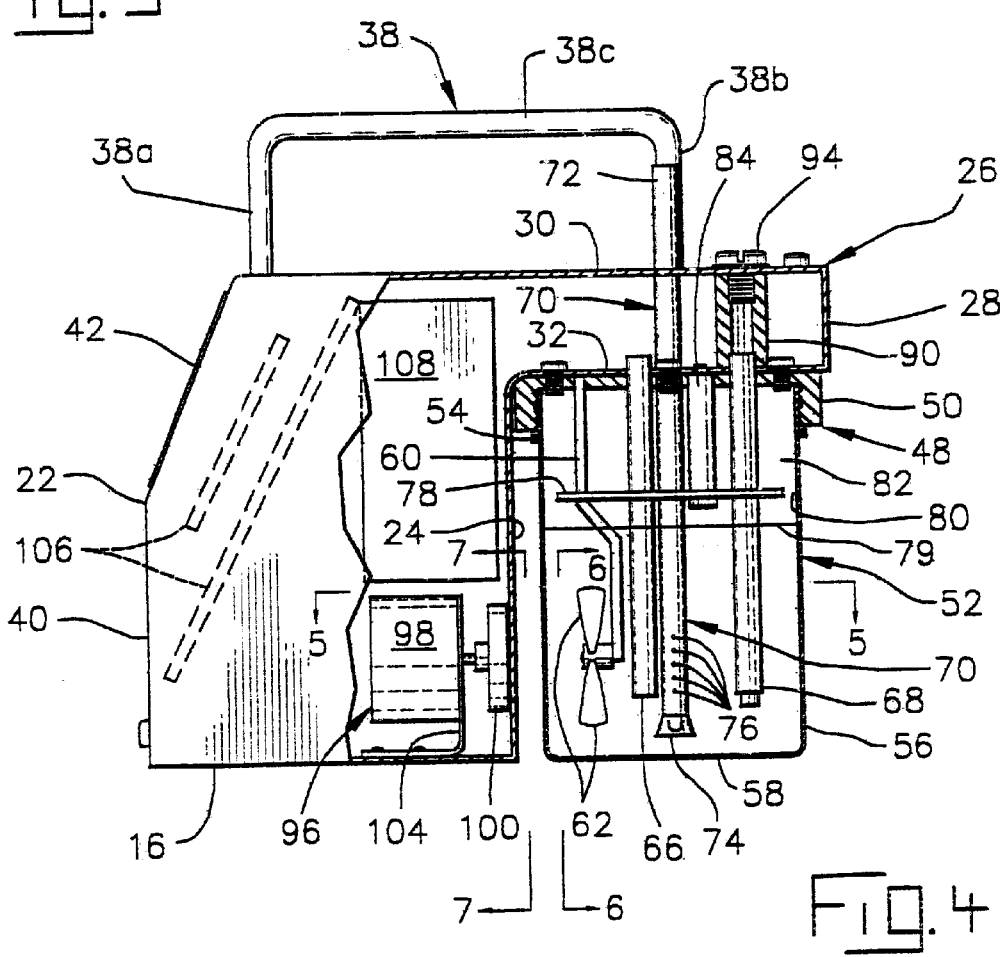
FIG. 4 is a partially broken away side view of the simulator like FIG. 1.

Circular jar lid 48 is secured to arm bottom 32 and includes an interiorly threaded circular lip 50. Plastic solution jar 52 includes a threaded upper end, and exterior bead 54 at the upper end below the threads, a cylindrical side wall 56 and a flat bottom 58. The top of jar 52 is threaded into lid 48 to seat bead 54 against the bottom of the lid, as shown in FIG. 4. In this position, the jar bottom 58 is coplanar with case bottom 16 so that when simulator 10 is placed on a horizontal surface both bottom 16 and 54 rest of the surface and support the simulator.

Arm 26 supports a number of components which extend downwardly from the arm into jar 52. Stirrer support rod 60 is mounted on lid 48 adjacent case front 24 and extends downwardly from the lid to an end (not illustrated) located a short distance above the bottom of the jar and extending toward case front 24. A pair of 180 degree-opposed stirrer vanes 62 are rotatably mounted on the lower end of rod 60 for rotation in the solution in the jar about a horizontal axis. A driven magnet 64 is mounted in the outer end of each vane 62. If desired, the magnets may be covered by a suitable protective covering which isolates the magnets from a solution in the jar. The vanes may be covered by an epoxy material.

Heater tube 66 extends through arm bottom 32 and lid 48 down into jar 56. Heater tube 66 carries a heater at the lower end thereof for heating the solution in the jar. The heater may be a resistance heater or other type of heater, including a small halogen light bulb. For a jar holding a 150 milliliter solution, the heater may have a 3 watt output.

Temperature sensor tube 68 likewise extends through arm bottom 32 and lid 48 down into the jar to a lower end adjacent the bottom of the jar. The sensor tube includes a solid state temperature sensor forming part of circuitry used to monitor the temperature of the solution in the jar. This circuitry (not illustrated) provides the temperature output reading for display 44 and also provides an actuation signal to control circuitry for the heater in tube 66 to actuate the heater when the temperature of the solution falls below a reference temperature.

Blow inlet tube 70 extends through arm 26 and lid 48 and includes an upper inlet end 72 above arm top 30 and to one side of handle 38 and a closed lower end 74 adjacent the bottom of the jar. A number of small diameter air dispersion holes 76 extend through the tube adjacent lower end 74 to disperse air blown through the openings into the solution in the jar and forms many small bubbles in the solution.

Figure 5:
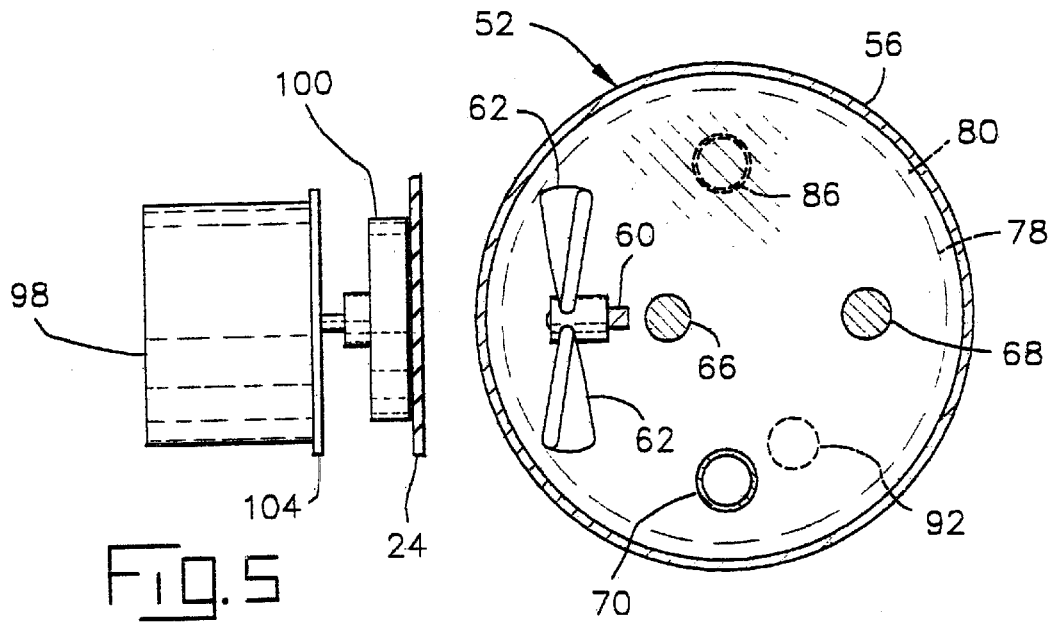
FIG. 5 is a sectional view taken along line 5—5 of FIG. 4.
Figure 6:
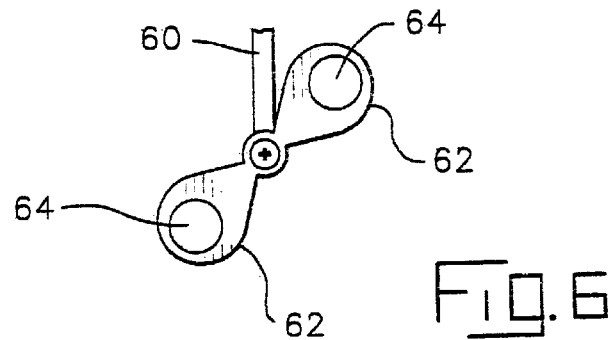
FIG. 6 is a view taken along line 6—6 of FIG. 5.
Figure 7:
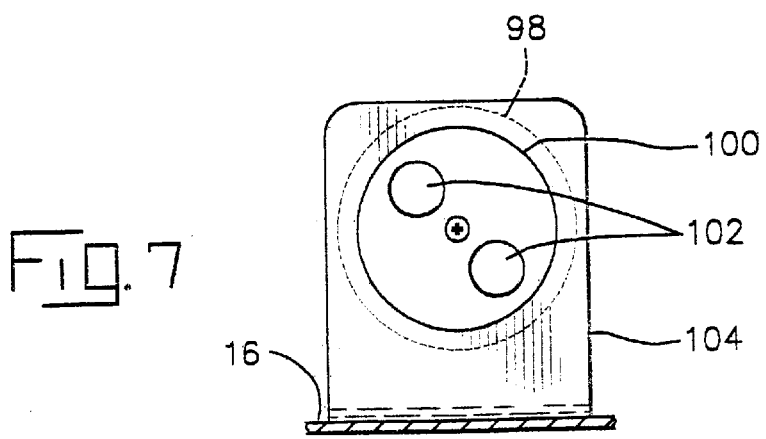
FIG. 7 is a view taken along line 7—7 of FIG. 4 with the side of the case not shown.

Rods 60, heater tube 66, sensor tube 68 and blow inlet tube 70 extend through openings formed in a circular baffle plate 78 located horizontally in the jar above the top surface 79 of the solution in the jar. The baffle plate is spaced inwardly from the jar side wall 56 to define a narrow circumferential gap 80 between the baffle plate and the side of the jar. See FIG. 5. The baffle plate defines a head space 82 in the jar located between the baffle and the lid. The baffle plate is supported by post 84 mounted on arm bottom 32 and extending through lid 48. Solution outlet tube 86 extends through arm 26 and lid 48 and includes an upper outlet end 88 projecting upwardly from the top of the arm to one side of handle 38, away from inlet end 72 of tube 70, and a lower inlet end (not illustrated) opening into head space 82.

Calibration port tube 90 extends through arm 26 and opens into the head space 82 above calibration port opening 92 formed in baffle plate 78. Threaded plug 94 normally closes the top of tube 90 at the top of arm 26. Plug 94 is removed to permit extension of a temperature probe through tube 90 and opening 92 and into the solution in the bottom of jar 52. The sensor is used to determine the temperature of the solution in the jar independently of the temperature circuits in the simulator.

Stirrer drive 96 is mounted on case bottom 16 adjacent front 24. The drive includes an electric motor 98 with a rotary disk 100 mounted on the output shaft of the motor. As illustrated in FIG. 4, the output disk is located immediately adjacent aluminum case front 24, a short distance inwardly from the front to permit free rotation by motor 98. Disk 100 includes two diametrically spaced drive permanent magnets 102. Motor 98 rotates disk 100 with magnets 102. The lines of force of magnets 102 extend through aluminum case front 24 and the plastic side wall 56 of jar 52 and are couple with stirrer driven magnets 64 so that the stirrer is rotated inside the jar in the same direction of rotation as the disk. The drive disk and stirrer are co-axial. Rotation of the angled stirrer vanes circulates the solution in the jar past heater tube 66 so that the entire solution is maintained at a desired temperature by the heater. Circulation of the solution in the jar also distributes the small bubbles of air flowed out from the lower end of blow inlet tube 70 into the solution to facilitate formation of an equilibrium concentration of alcohol vapor in bubble air. Electric motor 98 preferably rotates the stirrer at a speed of about 60 to 100 RPM. The stirrer is mounted close to the side of the jar adjacent the drive disk 100 in order to position the drive and driven magnets as close together as possible. As shown in FIG. 4, the stirrer drive motor 98 is mounted on bracket 104 secured to case bottom 16.

Electronic circuitry for monitoring the temperature of solution in jar 52, providing appropriate power as required to the heater in tube 66 and generating a visual output signal for display 44 is carried on circuit boards 106 mounted in case 12 adjacent back wall 22. This circuitry, and motor 98 may be powered by a rechargeable battery 108 mounted in case 12 above stirrer drive 96. Battery 108 is located close to case front 24 above stirrer drive 96 and under handle 38. This location of the battery, away from back wall 22 and as close as possible to jar 52 locates the center of gravity of simulator 10 under the handle 38 and close to the horizontal midpoint of the simulator, one-half the distance between back wall 22 and arm front 28. Location of the battery as illustrated stabilizes the simulator with jar 52 attached against tipping. Battery 108 cannot be lowered below the position illustrated because stirrer drive 96 must be located at the level of stirrer vanes 62 which are immersed in solution in the bottom of jar 52.

The simulator may be provided with a jack for connection to a power cable adapted to engage an external power source, including a direct current source, such as the battery of a motor vehicle or an alternating current source, such as 110 volt alternating 60 cycle power source. Battery 108 or the external power sources, if used, are connected to the circuitry for the simulator and motor 98 through on/off switch 46.

The operation of portable breath test simulator 10 will now be described. Prior to operation, a jar 52 filled with a water-ethyl alcohol solution of known concentration is mounted on lid 48 as illustrated in FIG. 4. The lid may include a resilient seal engaging the top of the jar to prevent leakage. The top of the solution in the jar 79 is located below baffle plate 78.

With the jar and solution in place and the simulator supported on a horizontal surface, an operator turns switch 46 on to actuate the simulator. Motor 98 is powered to rotate drive disk 100 and magnets 102 to rotate the stirrer vanes 62 in the jar through magnetic coupling between drive magnets 102 and driven magnets 64. The magnets are coupled together by lines of force which pass through the aluminum wall at case front 24 and the plastic side wall 56 of jar 52. Rotation of the angled stirrer vanes 62 circulates the solution in the bottom of the jar to move the solution past heater tube 66 and temperature sensing tube 68. Rotation of the stirrers maintain the solution in the jar at an even temperature.

As explained more fully in U.S. Pat. No. 4,407,152, the alcohol-water solution in jar 52 may have 1.21 grams of ethyl alcohol per liter of water to produce an effluent having a concentration of 0.100 grams of alcohol vapor per 210 liters of air at 34° C. In order to operate simulator 10 to test the accuracy of a breath test analyzer it is necessary to heat the alcohol-water solution to 34° C.

When the simulator is first actuated the solution is at a temperature below 34° C. The temperature sensor in tube 68 senses the low temperature and actuates the heater in tube 66 to supply heat to the solution. During heating, the temperature of the solution is monitored by the control circuitry and also by an operator viewing display 44. The stirrer circulates the solution in the jar and maintains the solution at a constant temperature during heating. When the display indicates the solution has reached a temperature of 34° C., the simulator may be used to calibrate breath test analyzers.

Breath test analyzers are calibrated by attaching a blow tube to upper end 72 of blow inlet tube 70. The blow tube preferably includes a breath test mouthpiece or trap that captures solids contained in the breath flowed through the tube to prevent solids from entering tube 70 and clogging dispersion holes 76. The mouthpiece may be of the type disclosed in Guth, U.S. Pat. No. 4,292,978. A discharge tube is mounted on the upper end 88 of outlet tube 86. The other end of this tube is mounted on the breath test inlet of the analyzer being tested.

The analyzer is tested by the operator blowing air into the mouthpiece, though the connecting tube, through tube 70 and out dispersion holes 76 at the bottom of tube 70. The bubbles rise up through the alcohol-water solution so that the air in the bubbles includes alcohol vapor and water vapor in equilibrium with the alcohol-water solution in the jar. The bubbles form an effluent which flows up from the solution past baffle plate 78 and into head space 82. The baffle plate prevents solution droplets from flowing into the headspace. The effluent closely simulates human breath and contains a precisely known concentration of alcohol vapor.

Blowing of air into jar 52 increases the pressure in the jar and flows the effluent in headspace 82 through outlet tube 86 and to the analyzer of being tested. The alcohol in the effluent is measured by the analyzer to generate an analyzer alcohol vapor readout. If the readout is high, the analyzer must be adjusted to lower the reading to the known alcohol concentration. If the analyzer is low, the analyzer must be adjusted to increase the readout. No adjustment is required if the readout is accurate.

Simulator 10 may be used to test the accuracy of all types of breath test analyzers, including pocket held preliminary test analyzers used in the field, automobile interlocks with breath test analyzers of the type attached to automobiles driven by individuals convicted of driving under the influence of alcohol and large console type breath test analyzers used to determine the breath alcohol with great accuracy.

Jar 52 may contain a 150 milliliters of water-alcohol solution. This solution is sufficiently large to conduct fifteen tests of small, preliminary breath test analyzers and a smaller number of tests of bench type breath test analyzers. The operator of simulator 10 keeps track of the number and types of tests performed using one solution in the jar to determine when it is necessary to replace the solution. At this time, the jar is simply unscrewed from lid 50 and the used solution and jar are discarded. A new jar, containing a fresh charge of water-alcohol solution, is mounted on the lid as described. The new solution is heated to the desired operating temperature, as described, to permit renewed testing using the new solution.

During operation of simulator 10 it may be desirable for the operator to confirm the temperature of the solution in jar 52. In this event, the operator removes plug 94 from calibration port tube 90 to permit insertion of a temperature probe or thermometer through calibration port tube 90 and tube opening 92 in the baffle plate and into the solution in the bottom of the jar to determine the temperature of the solution independently of the circuitry of simulator.

Simulator 10 is supported on a horizontal surface by bottom 58 of jar 52 and bottom 16 of case 12. The stirrer drive 96, circuit boards 106 and battery 108 are all located in case 12 to one side of the jar. This arrangement reduces the height of the simulator and increases the stability of the simulator to reduce the possibility of accidental tipping of the simulator. The location of stirrer drive 96 to one side of the jar eliminates conventional magnetic stirrers located at the bottom of a simulator container, thus reducing the height of the simulator and increasing stability.

Use of a magnetically driven agitator in jar 52 means that the interior of the jar is sealed without any moving parts extending into the jar. The sealed jar assures that alcohol vapor does not leak from the interior of the jar into the simulator. Vapor can injure bearings and other components located in case 12.

Simulator 10, with jar 52 attached and solution in the jar weighs about two pounds and is easily transported, facilitating on site analysis of breath test analyzers. Between uses of the simulator and during transport, the ends of a short tube are mounted on the upper ends of tubes 70 and 86 to close the interior of the jar and prevent leakage of solution from the jar.

Simulator 10 is intended for use with precharged jars, like jar 52, containing 150 millimeters of ethyl alcohol-water solution of desired concentration. Use of precharged jars facilitates field use of simulator 10 by permitting the operator to remove and discard jars with depleted solution and then mount a new jar, filled with solution of desired alcohol concentration. While we have illustrated and described a preferred embodiment of our invention, it is understood that this is capable of modification, and we therefore do not wish to be limited to the precise details set forth, but desire to avail ourselves of such changes and alterations as fall within the purview of the following claims.

What we claim as our invention:

1. A breath test simulator comprising; a case having a case top, a case bottom, a case front and an arm extending outwardly from the case front, the arm including an arm bottom above the case bottom, a jar mounting member on the arm bottom; a jar having an open top, a jar side wall, a jar bottom, and mounting structure at the jar top, said jar mounting structure removably engaging said jar mounting member to mount the jar on the arm, the height of the jar and the height of the jar mounting member above the case bottom being about the same so that the jar bottom and the case bottom are at essentially the same level when the jar is mounted on the arm and both the case bottom and the jar bottom support the simulator; a water-alcohol solution in the jar; a stirrer in the jar; a stirrer drive for moving the stirrer; a gas inlet device extending into the solution; and a gas outlet device for flowing gas out from the jar.

2. The breath test simulator as in claim 1 wherein the stirrer drive comprises an electric motor in the case and including a battery for the motor in the case, the battery located adjacent the case front.

3. The breath test simulator as in claim 2 wherein said electric motor is located below the battery and adjacent said case front; and including a drive magnet rotatable by the motor; a stirrer support mounted on the arm and extending into the jar adjacent said motor, said stirrer rotatably mounted on said stirrer support and including a driven magnet, whereby said drive and driven magnets are magnetically coupled and rotation of said drive magnet by said motor rotates said driven magnet and stirrer in the jar.

4. The breath test simulator as in claim 3 wherein said case front comprises a nonmagnetic panel.

5. The breath test simulator as in claim 4 wherein said jar comprises a nonmagnetic side wall.

6. The breath test simulator as in claim 2 including a handle mounted on the case above the center of gravity of the simulator.

7. The breath test simulator as in claim 6 wherein said case includes a case top; said arm includes an arm top; and said handle includes a generally horizontal grip portion having opposed ends, one arm end located above said case top and the other arm end located above on said arm top.

8. The breath test simulator as in claim 6 including a heater in the solution, heater circuitry connected to the heater for actuating the heater to heat the solution in the jar to a desired temperature; a temperature sensor to sense the temperature of the solution; a temperature display on the case; temperature circuitry for receiving a signal from the temperature sensor and generating a signal to the display indicating the temperature of the solution in the jar, said case including a back wall, said circuitry located in the case adjacent said back wall.

9. A breath test simulator including an aeration chamber having a bottom and a circumferential side wall, said side wall formed from a nonmagnetic material, a breath test solution in the chamber, a first device for flowing gas into the solution in the chamber; a second device for flowing gas out from the chamber; an agitator support located in the chamber adjacent the side wall thereof; an agitator rotatably mounted on the support, the agitator including a first driven magnet; an electric motor located outwardly of the container adjacent the container side wall and above the chamber bottom, the motor including a drive shaft; a first drive magnet mounted on the drive shaft for rotation therewith, whereby rotation of the drive motor rotates the drive magnet, and the rotating drive magnet is magnetically coupled with the driven magnet through the side wall of the container to rotate the drive magnet and agitator in the solution.

10. The breath test simulator as in claim 9 including a heater in the chamber; a temperature sensor in the chamber, a power source for actuating the heater; and circuitry responsive to a signal from the temperature sensor for actuating the heater when the temperature of the solution is below a desired temperature.

11. The breath test simulator as in claim 9 including a case having a portion formed from nonmagnetic material located between the drive magnet and the chamber, said motor mounted on the case.

12. The breath test simulator as in claim 9 including a case formed from sheet aluminum, the case having a case top, a case bottom, a case front and an arm extending outwardly from the case front, the arm including an arm bottom above the case bottom; a jar mounting member on the jar bottom; said aeration chamber comprising a jar having an open mouth, jar mounting structure adjacent the mouth and a jar bottom, said jar mounting structure removably engaging the jar mounting member on the arm to secure the jar to the case with the jar bottom and the case bottom located at essentially the same level so that both support the simulator.

13. The breath test simulator as in claim 12 including a battery in the case; a handle on the top of the case, said handle located above the center of gravity of the breath test simulator.

14. The breath test simulator as in claim 9 including a second driven magnet and a second drive magnet, said agitator including a pair of opposed, angled vanes with one drive magnet mounted in each of said vanes; and including a rotatable member mounted on said motor drive shafts said drive magnets secured to said rotatable member.

15. The breath test simulator as in claim 9 wherein said agitator and said drive shaft rotate about the same axis.

\* \* \* \* \*